(12) United States Patent
Gasper (10) Patent No.: US 7,206,505 B2
(45) Date of Patent: Apr. 17, 2007

(54) VOLATIZER WITH INTEGRATED THERMAL CUTOFF

(75) Inventor: Thomas P. Gasper, Germantown, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 117 days.

(21) Appl. No.: 10/879,312

(22) Filed: Jun. 29, 2004

(65) Prior Publication Data

US 2005/0286876 A1 Dec. 29, 2005

(51) Int. Cl.
*F24F 6/00* (2006.01)
*H01H 85/02* (2006.01)

(52) U.S. Cl. .................. 392/392; 392/390; 337/186

(58) Field of Classification Search ............... 392/386, 392/390, 391, 392, 393, 394, 395; 422/120, 422/125; 337/186, 190, 198; 338/230, 276, 338/317, 324

See application file for complete search history.

(56) References Cited

U.S. PATENT DOCUMENTS

| | | |
|---|---|---|
| 899,749 A | 9/1908 | Mears |
| 2,029,097 A | 1/1936 | Garner |
| 2,726,302 A | 12/1955 | Levy |
| 2,790,049 A | 4/1957 | McAlister |
| 3,201,549 A | 8/1965 | Lowe |
| 3,423,567 A | 1/1969 | Mills |
| 3,827,014 A | 7/1974 | Wehl |
| 4,134,092 A | 1/1979 | Lavigne et al. |
| 4,208,645 A | 6/1980 | Harmon et al. |
| 4,255,736 A | 3/1981 | Kelley et al. |
| 4,306,213 A | 12/1981 | Rose |
| 4,366,462 A | 12/1982 | Hollweck |
| 4,527,144 A | 7/1985 | Arikawa |
| 4,533,897 A | 8/1985 | Olson et al. |
| 4,780,286 A | 10/1988 | Parent et al. |
| 4,829,280 A * | 5/1989 | Blackburn et al. .......... 337/299 |
| 4,929,922 A | 5/1990 | Hollweck |
| 5,825,278 A | 10/1998 | Reid et al. |
| 5,937,140 A * | 8/1999 | Leonard et al. ............. 392/392 |
| 5,982,270 A | 11/1999 | Wolfe, Jr. et al. |
| 6,097,881 A * | 8/2000 | DeWitt et al. .............. 392/392 |
| 6,204,747 B1 | 3/2001 | Kitchens |
| 6,348,851 B1 | 2/2002 | Wyser et al. |
| 6,478,440 B1 * | 11/2002 | Jaworski et al. ............. 362/96 |

FOREIGN PATENT DOCUMENTS

| | | |
|---|---|---|
| EP | 0 727 799 | 8/1996 |
| WO | WO 98/11924 | 3/1998 |

OTHER PUBLICATIONS

International Search Report and Written Opinion, Appl. No. PCT/US2005/023036 dated Oct. 24, 2005.

* cited by examiner

*Primary Examiner*—Sang Paik (57) ABSTRACT

A volatizer has a case that deforms to interrupt electrical current flow through an internal heating element.

22 Claims, 5 Drawing Sheets

VOLATIZER WITH INTEGRATED THERMAL CUTOFF

FIELD OF THE INVENTION

The invention relates generally to volatizers, and more particularly to thermal cutoffs for volatizers.

BACKGROUND OF THE INVENTION

The volatizer is a plug-in diffuser for such active materials as fragrances and air fresheners, and uses replaceable cartridges of volatile material to be dispensed. In these devices, a resistance heater is disposed in a housing, out of which electrical prongs extend directly. When the prongs are plugged into a wall socket, the resistance heater generates heat. Volatile material, such as fragrance or an insect repellant to be emitted into the air is maintained, either in liquid, gel or solid form, in close proximity to the heater. As the heater heats the substance, controlled amounts are vaporized or "volatized" and emitted into the surrounding atmosphere.

These devices are typically used in households, particularly in kitchens and bathrooms, because they provide a continuous, controlled flow of desired volatile material into the air. They are inexpensive and are made in large quantities as compared to other consumer products.

In many consumer products, stand-alone thermal cutoff devices (TCO's) are used to prevent overheating. Companies manufacture stand-alone thermal cutoffs in a wide variety of configurations that can be easily integrated into consumer products such as toasters, hot plates, coffee makers, toaster-ovens, hair dryers, and the like by consumer product manufacturers.

Using a stand-alone TCO in a consumer device increases its cost to manufacture and increases assembly time. Manufacturing cost and assembly time may not be a significant issue for larger and more expensive consumer products such as toasters, hot-plates, coffee makers, toaster-ovens and hair dryers. Manufacturing cost an assembly time are significant issue with smaller, low cost items such as volatizers.

What is needed is a volatizer with an integrated thermal cutoff that avoids the costs of a separate stand-alone thermal cutoff. What is also needed is a way of incorporating the thermal cutoff into the volatizer that permits faster assembly. It is an object of this invention to provide such a volatizer.

SUMMARY OF THE INVENTION

A volatizer or thermal diffuser of an active material is provided, comprising a housing of a suitable material, such as polypropylene, an electric resistance heater, such as a metal oxide resistor, and associated electric circuitry including an integrated thermal cutoff composed of a conductive armature in a tension state held in electrical contact by the volatizer housing itself.

The purpose of the integrated thermal cutoff is to use the volatizer's own unique design and materials to create a circuit that will open and turn off the heater without adding a special stand-alone thermal cutoff. This arrangement takes advantage of the deformation that will occur in the plastic housing material of the volatizer during an overheating condition. By using a spring loaded contact armature that is held in place by the plastic housing, the armature will move from its contact position and will open the circuit when the device overheats and the plastic housing is deformed.

In accordance with a first aspect of the invention, a volatizer is provided having a case, electrical prongs extending from the case, and a thermal heating element disposed in the case. The case is configured to support and heat volatile material. The case is also configured to deflect upon excessive heating of the thermal heating element and break an internal electrical connection to the thermal heating element.

The volatizer may include a spring loaded metal armature, configured to make electrical contact with the thermal heating element. The armature may be held in contact with the thermal heating element by the case. The armature and electrical prongs may be fixed to the case. The armature and electrical prongs may have a case retaining means. The electrical prongs may include two electrical prongs configured to be inserted into an electrical receptacle. The electrical prongs may be configured to be inserted into a 120V household electrical receptacle.

In accordance with a second aspect of the invention, a volatizer is provided having a case, a first power blade and a second power blade supported by the case, a first bus bar and a second bus bar supported in the case, and a thermal heating element supported in the case. The case is configured to support and heat volatile material and deflect upon excessive heat and function as a thermal cutoff by breaking an internal electrical connection to the thermal heating element.

The case may be configured to support and heat volatile material selected from a group comprising a liquid, a gel and a liquid impregnated solid. The case may be configured to support and heat volatile material selected from a group comprising a fragrance, a medicinal, a sanitizer, a deodorant, a pest repellent, a disinfectant, an aroma therapy formulation, a household cleaning material, a perfume, a therapeutic liquid, an insecticide, and a decongestant. The first bus bar may include a heating element retainer and an armature spring configured to be pressed into a tensioned state by the case, such that the case holds the armature spring into electrical contact with the heating element retainer. When assembled, the case may hold the armature spring in physical contact with the thermal heating element, creating an electrical connection between the armature spring and the thermal heating element. During volatizing operation the first power blade may make electrical contact with the first bus bar, the first bus bar may make electrical contact with the thermal heating element, the thermal heating element may make electrical contact with the second bus bar, and the second bus bar may make electrical contact with the second power blade, creating an electrical path from the first power blade to the second power blade. The first power blade may make electrical contact with the armature spring, the armature spring may make electrical contact with the heating element retainer, and the heating element retainer may make electrical contact with the thermal heating element, creating an electrical path from the first power blade to the thermal heating element when the case is assembled. The first power blade may be in contact with the armature spring, the armature spring may be in contact with the thermal heating element, and the thermal heating element may be in contact with the heating element retainer.

In accordance with a third aspect of the invention, a fragrance releaser is provided having a case configured to deflect upon excessive heat and break an internal electrical connection. The case includes a plug deck including a first power blade and a second power blade, and a housing coupled to the plug deck. The housing supports a first bus bar, a second bus bar, and a heating element. The first bus bar includes an armature spring and a heating element retainer.

The case is configured to support and heat volatile fragrance, the volatile fragrance being a liquid, a gel or a liquid impregnated solid.

The power blades may be configured to be press fit into the plug deck. The housing may include an armature mount, a heating element retainer mount, and a second bus bar mount. The armature spring may be configured to be press fit into the armature mount, the heating element retainer may be configured to be press fit into the heating element retainer mount, and the second bus bar may be configured to be press fit into the second bus bar mount. The heating element may have a first end and a second end, the second bus bar may be configured to receive the second end, the heating element retainer may be configured to receive the first end, and the heating element may be configured to be press fit into the heating element retainer and the second bus bar. The housing may include an armature spring boss configured to hold the armature spring in a tension state by pushing the armature spring away from the heating element. The plug deck may include an armature spring actuator configured to push the armature spring into physical contact with the heating element when the case is assembled. The distance between the armature spring actuator and the heating element may be between 0.3 and 0.7 millimeters when the case is assembled. The armature spring may be formed in an arc such that when the case is assembled the thermal cutoff function will be achieved despite a manufacturing difference of +/−10% in the size of the armature spring actuator, armature spring boss, armature spring mount, heating element retainer mount, plug deck or housing.

DETAILED DESCRIPTION OF THE PREFERRED EMBODIMENTS

A "volatile material" is defined as a liquid, gel or liquid impregnated solid that incorporates at least one active ingredient configured to be volatized by application of heat. The active ingredient may be one of many substances, generally defined by its purpose, including but not limited to fragrances, air fresheners, perfumes, deodorizers, household cleaning materials, odor eliminators, odor counteractants, insecticides, insect repellants, herbal substances, medicinal substances, therapeutic liquids, decongestants, disinfectants, sanitizers, mood enhancers, aroma therapy compositions, and mixtures thereof.

"Power blades" or "electrical prongs" refer to any rigid conductive member, designed to mechanically and electrically engage a standard electrical outlet. Electrical outlets may provide power at different voltages and frequencies, and accommodate varying numbers of power blades. The power blades may also be of different shapes. These variances will necessitate changes in the number, disposition and shape of the power blades in order for the volatizer to function in different geographic regions. At least 13 types of household plugs exist worldwide, varying by power blade number, shape, location and orientation. Outlets may provide voltages of 110 to 240V, at frequencies ranging from 50 to 60 Hz. However all plugs and outlets perform the same basic function, to convey electrical power from an electrical outlet to a plugged in electrical device via a set of power blades that are part of the electrical device.

A "volatizer" (also known as a "volatile actives dispenser") heats a volatile material to volatize its active ingredient and accomplish a desired purpose. The purpose varies considerably and will drive the choice of volatile material, whether it be eliminating or disguising odors (such as air fresheners, scents or fragrances), medicinal (such as decongestants), or behavioral (such as pest-control chemicals). Plug-in diffusers, plug-in fragrance releasers, and insecticide heaters are examples of typical volatizers.

Figure 1:
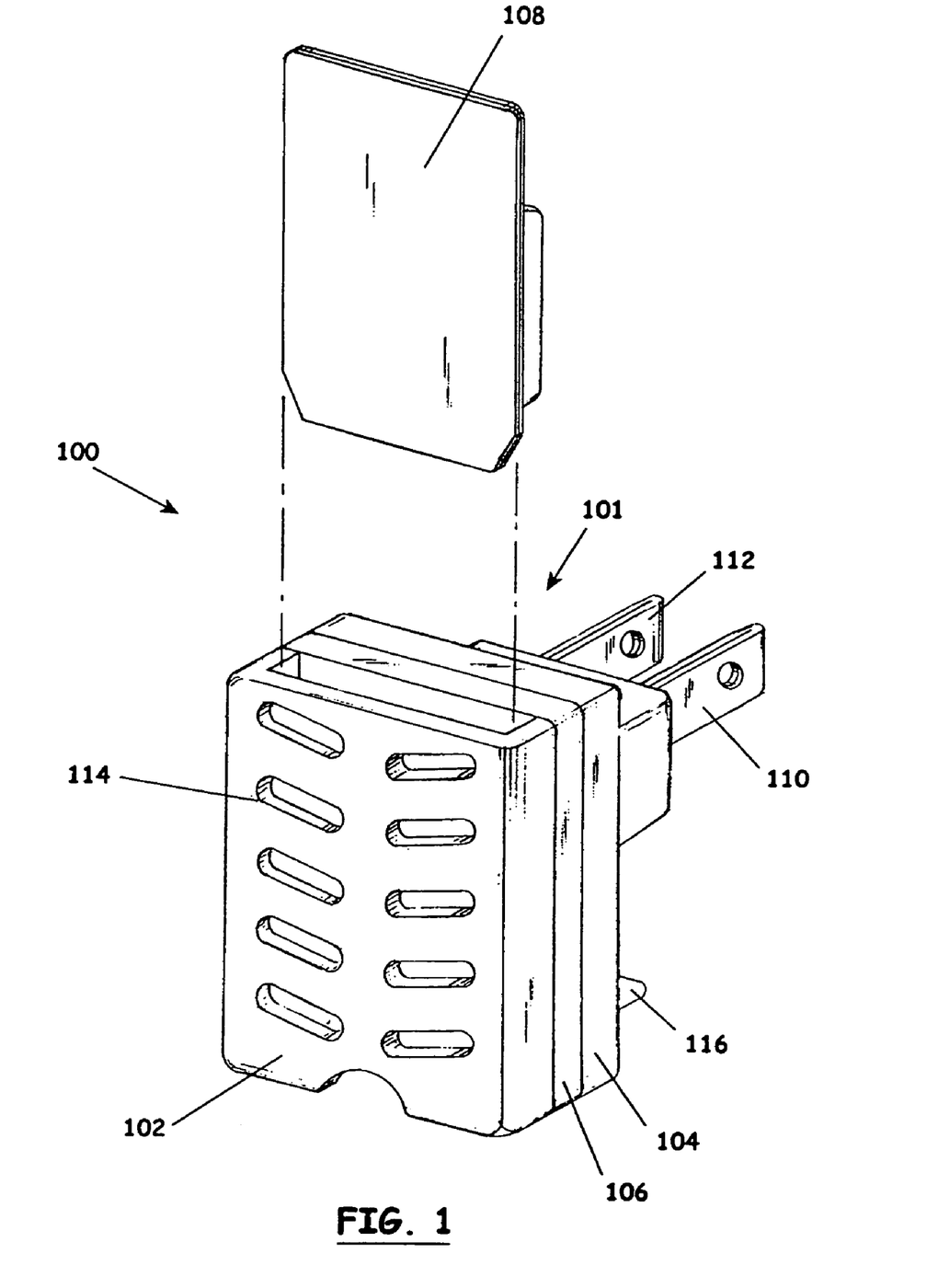
FIG. 1 is a front perspective partially exploded view of an assembled volatizer having an integral thermal cutoff in accordance with the present invention. The fragrance refill pack is shown uninserted.
Figure 2:
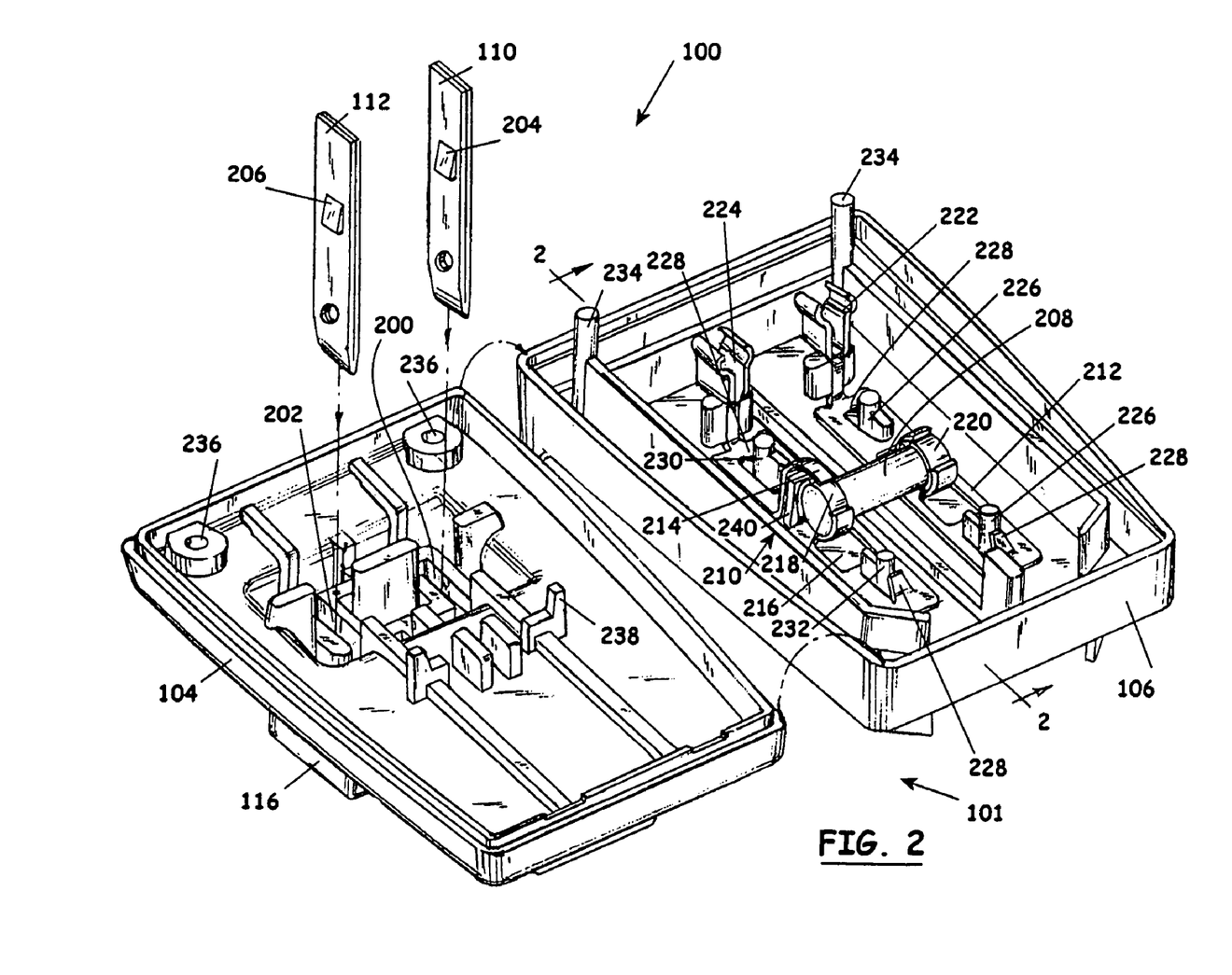
FIG. 2 is a perspective view of a volatizer partially assembled showing the case and electrical components.

FIG. 1 shows a volatizer 100. In this embodiment the volatizer is a fragrance releaser. The volatizer includes a case 101 and power blades 110,112. The case includes a faceplate 102, a plug deck 104, a main housing 106 and electrical components (FIG. 2). The case 101 is configured to contain and heat volatile material 108. The power blades 110,112 are configured to engage an electrical outlet.

The volatile material 108 can be seen above the volatizer 100 in the process of insertion between the faceplate 102 and main housing 106. Volatile material 108 is not a part of volatizer 100, but is configured to be supported in and heated by the volatizer. The volatile material 108 is shown in a vertical orientation near the front of the case; however, the volatile material may be located near the top, bottom or back of the case. It is not necessary to have a separate faceplate 102; the plug deck 104 or main housing 106 may be fashioned with a suitable enclosure to contain the volatile material 108. Alternatively, the case 101 may be made of one continuous piece, as long as it can contain the electrical components and volatile material 108.

The first power blade 110 and second power blade 112 extend rearwardly from the volatizer. The power blades 110,112 are parallel and orthogonal to the rear surface of the plug deck 104. The preferred embodiment is shown with two flat parallel power blades which would insert into the holes in a standard U.S. non-grounded or grounded 120V/60 Hz electrical outlet.

In the preferred embodiment the faceplate 102 is press fit onto the main housing 106, however the faceplate may be screwed or otherwise attached to the main housing. The faceplate serves to contain the volatile material 108 securely during the heating process. Vents 114 on the faceplate allow free movement of the diffused gas from the heated volatile material 108 into the atmosphere.

The preferred embodiment of the volatizer is of the plug-in variety, not requiring an electrical cord. The power blades 110,112 are inserted into an electrical outlet such that the volatizer 100 fits flush against the wall. To restrict tipping of the volatizer a stabilizer 116 may be integrated into the plug deck 104 such that the contact points of the volatizer with the wall are not limited to the power blades 110,112.

The volatizer 100 is shown partially assembled in FIG. 2, with internal electrical components press fit in place. The case 101 is separated into its principal sections, the plug deck 104 and the main housing 106. The electrical components in the plug deck 104 include the first power blade 110 and the second power blade 112. The electrical components in the main housing 106 include a first bus bar 210, a second bus bar 212, and a thermal heating element 208. The first bus bar includes an armature 214 and a heating element retainer 216. The thermal heating element 208 has a first end 218 and a second end 220. The plug deck 104 and main housing 106 are molded so as to give strength to the case, and provide support and mounting points for the electrical components. The plug deck includes an armature actuator 238 and the main housing includes an armature boss 240. The armature actuator and armature boss are configured to bring the armature 214 into electrical contact with the other electrical components and create an electronic circuit when the case 101 is assembled.

During assembly of the case 101, the main housing 106 is pressed into the plug deck 104, which makes the armature actuator 238 press against the spring loaded armature (or "armature spring") 214. When fully assembled, the actuator pushes the armature against the first end 218 of the heating element 208. This completes an electrical path leading from the first power blade 110, through the armature 214, through the heating element 208, through the second bus bar 212, through the second power blade 112. Alternatively, the armature 214 could be lengthened or shortened and the armature actuator 238 relocated such that the armature actuator would press the armature against the heating element retainer 216 instead, and provide a similar electrical path leading from the first power blade 110 to the second power blade 112 via the heating element 208. In both alternatives, the case itself (the plug deck 104) pushes the armature to make an electrical connection.

The preferred embodiment uses press fit components to minimize assembly time and product cost, since extra retaining means are not necessary. The power blades 110,112 are shown just before insertion into the plug deck 104. The power blades 110,112 are inserted into the plug deck 104 through blade apertures 200,202 until their movement is stopped by blade bosses 204,206.

FIG. 2 shows all the other electronic elements after having been press fit into the main housing 106 on their respective mounts. The thermal heating element 208 is held securely by press fitting into the first bus bar 210 and the second bus bar 212. The armature and heating element retainer are not in physical or electrical contact until the case is assembled. The first end 218 of the heating element 208 is clamped by the heating element retainer 216. The second end 220 of the heating element 208 is clamped by the second bus bar 212. At the end of each bus bar 210,212 is a power blade clamp 222,224. When the case is assembled, the power blades 110,112 will be pressed into their respective power blade clamps 224,222, creating a physical and electrical connection.

The second bus bar 212 is press fit into the main housing 106 onto second bus bar mounts 226. The second bus bar is secured in place by bus bar clips 228 that press against the mounts 226. Similarly, the armature 214 is press fit into the main housing 106 onto an armature mount 230, and the heating element retainer 216 is press fit into the main housing 106 onto a heating element retainer mount 232. The armature and the heating element retainer are secured in place by bus bar clips 228.

The assembly process is as follows: The power blades 110,112 are press fit into the plug deck 104. The second bus bar 212, the armature 214 and heating element retainer are press fit into the main housing 106. The heating element 208 is press fit into the heating element retainer 216 and the second bus bar 212. The plug deck is turned 180 degrees as shown by the curved dashed arrows in FIG. 2 and press fit onto the main housing 106. This is facilitated by the main housing mounts 234 which align axially with and insert into the main housing insertion holes 236.

Additionally, the preferred embodiment includes a support for the armature 214 so that the armature keeps its arced shape. The armature spring boss 240 provides this function, extending inward from the main housing 106 toward the armature 214 from underneath the armature. Thus, when assembled, the armature boss 240 will flex the armature 214 upward, while the armature actuator 238 pushed the end of the armature downward. The combination of these two pressures will keep the armature in the required tension state.

Figure 3:
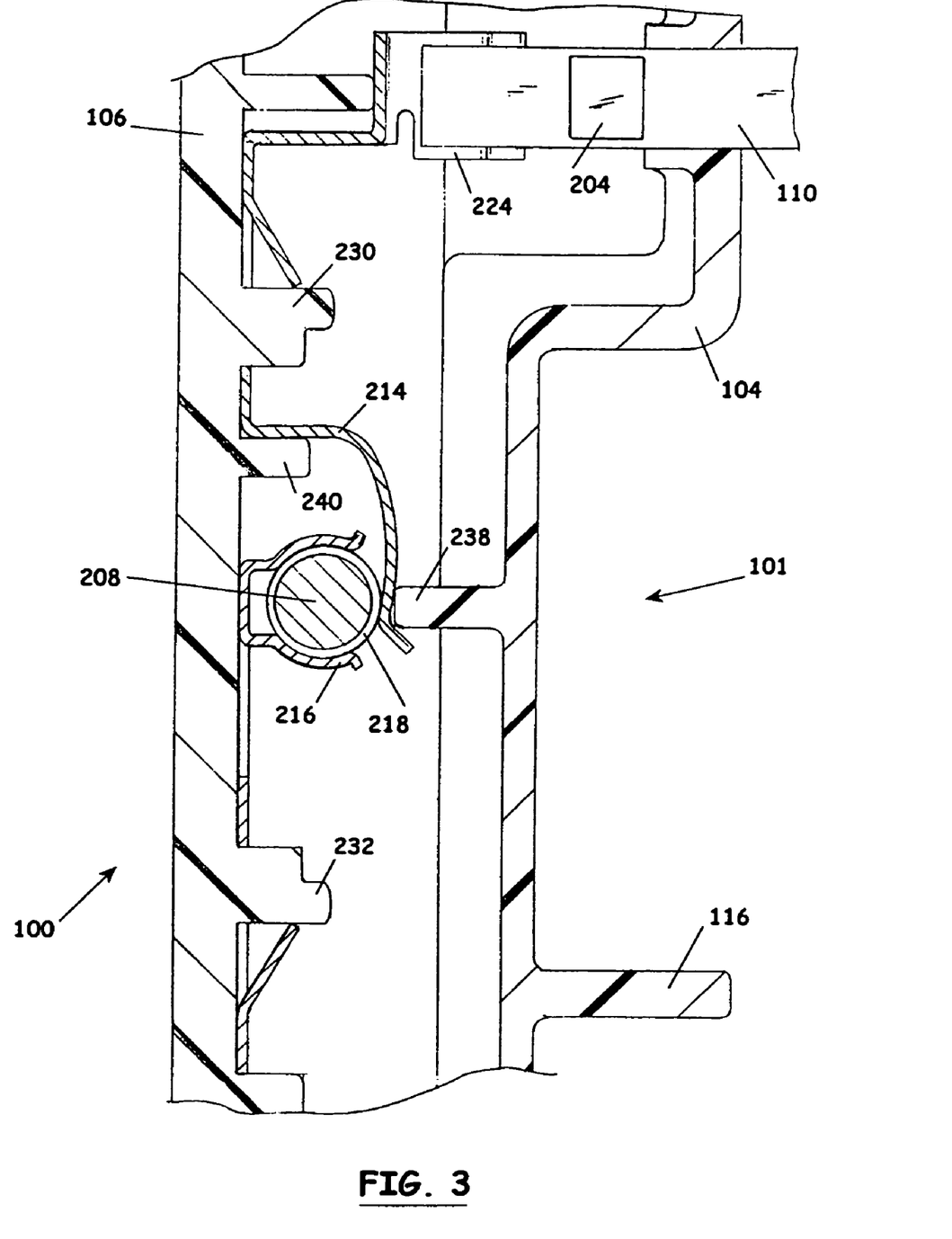
FIG. 3 is a partial cross section view (taken at line 2—2 of FIG. 2) of a volatizer showing the armature in working (electrically contacting) position.

FIG. 3 shows a closer view of the volatizer 100 fully assembled in operating condition. The armature actuator 238 is pressing the armature 214 against the first end 218 of the heating element 208. The armature boss 240 keeps the armature 214 in tension against the armature actuator 238. The electrical path of first power blade 110 to armature 214 to first end 218 can be clearly discerned.

Figure 4:
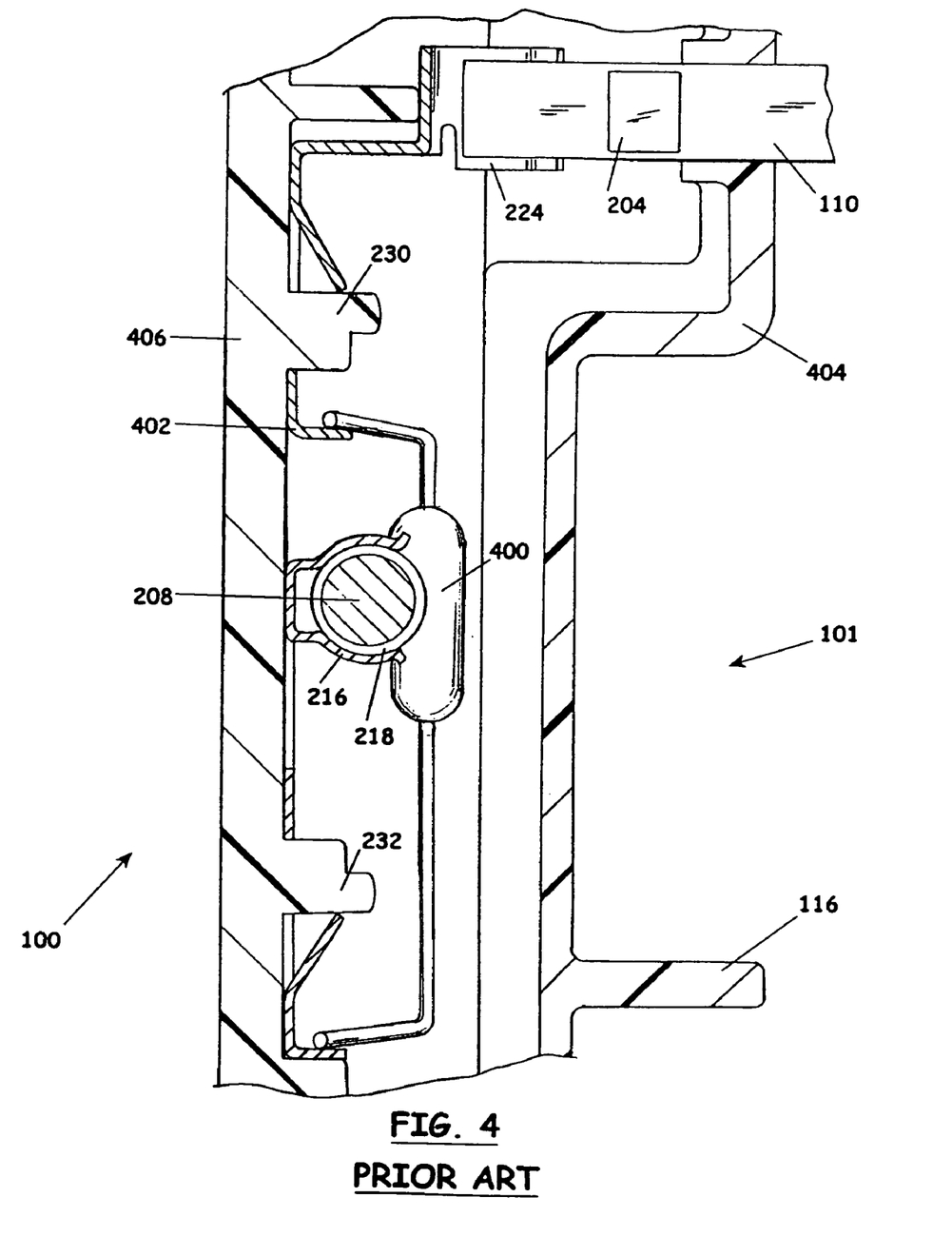
FIG. 4 is a partial cross section view of an alternative volatizer having a stand-alone thermal cutoff. In this configuration, a stand-alone thermal cutoff has been substituted for the armature arrangement to illustrate the differences between a volatizer employing a stand-alone thermal cutoff and a volatizer with an integral thermal cutoff in accordance with the claimed invention.

FIG. 4 illustrates another volatizer using a stand-alone thermal cutoff. The only differences between it an a volatizer with an integrated thermal cutoff, such as volatizer 100 shown in FIGS. 1, 2, 3 and 5 include the addition of certain small integrated thermal cutoff structures that replace the stand-alone thermal cutoff. These differences are explained below. For this reason, a complete set of FIGURES showing the structure of the volatizer of FIG. 4 is duplicative and has not been provided herewith.

In the volatizer of FIG. 4, a stand-alone thermal cutoff 400 bridges between a first power blade holder 402 and the heating element retainer 216. The stand-alone thermal cutoff 400 is electrically and mechanically fixed to the first power blade holder 402 and to the heating element retainer 216.

The first power blade holder 402 has two functions: (1) restraining the first power blade 110 and (2) making electrical contact between the first power blade and the stand-alone thermal cutoff 400.

Note the FIG. 4 electrical path runs from the first power blade 110 to the first power blade holder 402 to the stand-alone thermal cutoff 400 to the heating element retainer 216 to the first end 218 of the heating element 208. In the device (FIG. 2), the electrical path runs from the first power blade 110 to the armature 214, to the first end 218 of the heating element 208.

Figure 5:
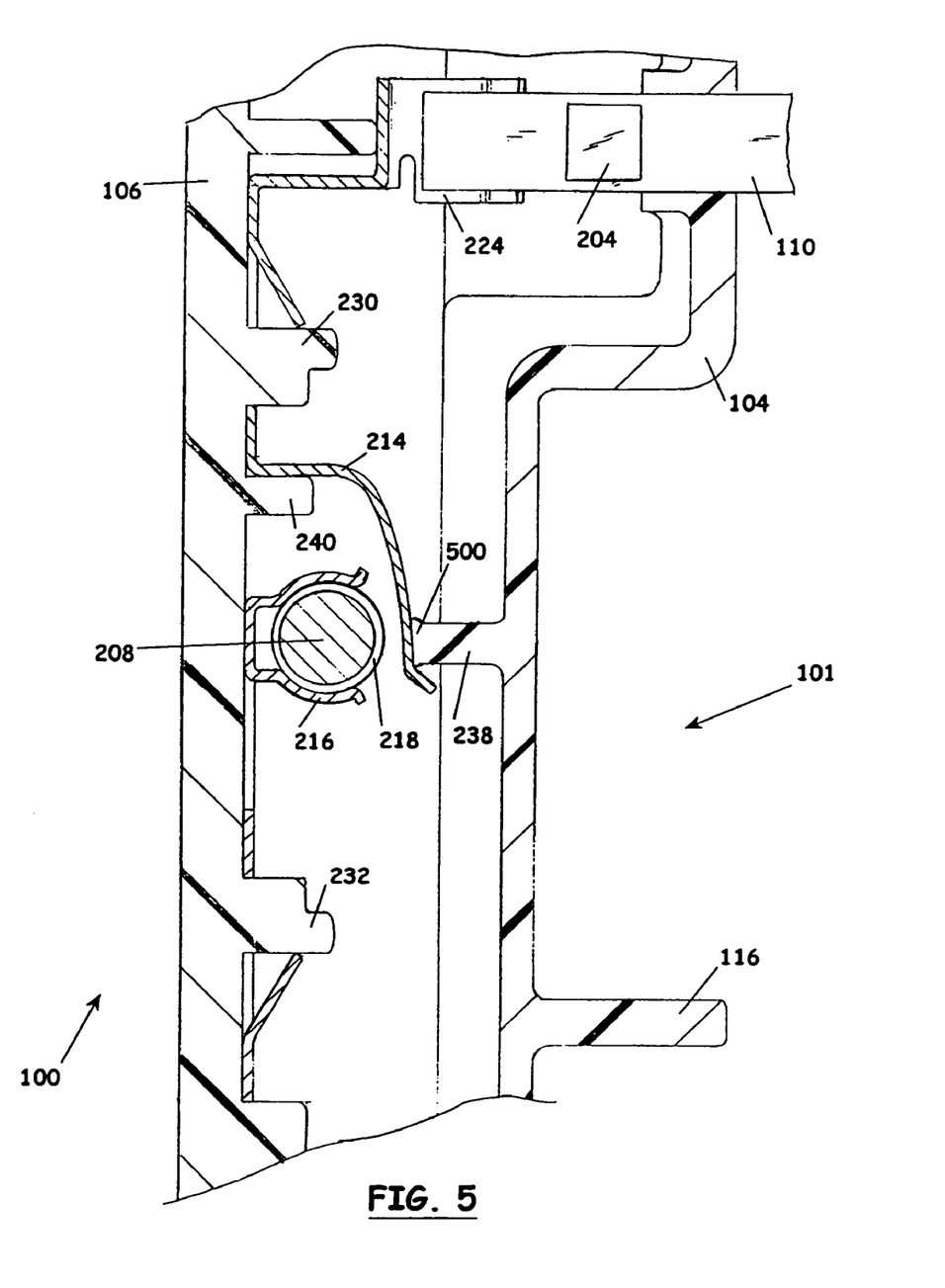
FIG. 5 is a partial cross section view (taken at line 2—2 of FIG. 2) of a volatizer showing the armature in thermal cutoff (electrically non-contacting) position after deformation of the case.

The first power blade holder 402 (FIG. 4) differs from the armature 214 (FIGS. 1–3, 5) in that the armature has three functions: (1) the armature restrains the first power blade 110, similarly to the function of the first power blade holder 402, (2) the armature makes electrical contact between the first power blade 110 and the first end 218 of the heating element 208, and (3) the armature and associated structures function as a thermal cutoff when the case 101 deforms (FIG. 5).

The armature 214 is longer than the first power blade holder 402, extending upward and laterally toward but not touching the first end 218 of the heating element 208.

The armature touches the heating element, making the electrical connection between power blade 110 and element 208 only when the case is assembled. In contrast, stand-alone thermal cutoff 400 completes an electrical connection between power blade 110 and element 208 even when the case is not assembled. Stand-alone thermal cutoff 400 (FIG. 4) is preassembled, whereas the integrated thermal cutoff of the claimed invention (FIGS. 1–3, 5) is assembled as the case is assembled.

The volatizer represented by the cross sectional view of FIG. 4 differs from the volatizer of FIGS. 1–3 and 5 in only a couple minor details: The back section 404 of the case in FIG. 4 does not include an armature actuator 238. The front section 406 of the case in FIG. 4 does not have an armature boss 240. In all other respects the volatizer with integrated thermal cutoff of FIGS. 1–3 and 5 is identical to the volatizer with stand-alone thermal cutoff of FIG. 4.

In an overheating situation, the stand-alone thermal cutoff 400 of FIG. 4 breaks (or opens) the electrical circuit between power blade 110 and thermal element 208 and stops the flow of electricity. This breaking occurs inside the body of stand-alone thermal cutoff 400. It does not require any mechanical interaction with any other components of the FIG. 4 volatizer. In this sense thermal cutoff 400 "stands alone", unlike the integrated thermal cutoff. The stand-alone thermal cutoff 400 is an additional self-contained part that is purchased and installed during volatizer assembly.

FIG. 5 shows how the volatizer case deforms when the assembled volatizer 100 overheats. The deformation occurs at the end 500 of the armature actuator 238, where the plastic melts slightly, allowing the armature 214 to relax partially from its tension state and move away from the first end 218 of the heating element 208. The movement of the armature 214 away from the heating element 208 breaks the physical and electrical contact of the armature and the heating element. The heating element 208 is no longer energized and will cool accordingly, before damage is done to the case or surrounding area. In the preferred embodiment the plug deck deforms. The main housing may deform as well as (or instead of) the plug deck.

Due to the spring constant of the armature 214, the supporting pressure of the armature boss 240, and counteracting pressure of the armature actuator 238, when either the main housing 106 or plug deck 104 soften due to overheating, the armature 214 will naturally move away from the heating element 208. The need for case deformation requires the plug deck or main housing to be manufactured of a heat deformable substance such as polypropylene.

There are alternative arrangements for the preferred embodiments such as locating the volatile material above, behind or below the heating element. Another arrangement may have a single molded piece of deformable housing that replaces the combination of faceplate, plug deck and main housing. A further arrangement may simplify the electronic elements to two pieces, with the first power blade and armature combined into one piece, and the heating element retainer, heating element, second bus bar and second power blade combined into the second piece.

It will be understood that changes in the details, materials, steps, and arrangements of parts which have been described and illustrated to explain the nature of the invention will occur to and may be made by those skilled in the art upon a reading of this disclosure within the principles and scope of the invention. The foregoing description illustrates the preferred embodiment or embodiments of the invention. Concepts based upon the description may be employed in other embodiments, however, without departing from the scope of the invention. Accordingly, the following claims are intended to protect the invention broadly as well as in the specific form or forms shown.

INDUSTRIAL APPLICABILITY

A volatizer is disclosed having a case that deforms to interrupt current flow through the volatizer when the volatizer overheats. This arrangement reduces the cost of the volatizer by eliminating a stand-alone thermal cutoff. In addition, the design also provides a volatizer that is easier to assemble and has fewer parts.

I claim:

1. A volatizer comprising:
   a case having a thermally conductive housing;
   electrical connections extending from the case;
   a thermal heating element disposed in the case; and
   a spring loaded metal armature disposed in the case and configured to make an electrical connection and physical contact with the thermal heating element,
   wherein the case is configured to support a volatile material, and
   wherein the thermally conductive housing of the case is configured to deform upon excessive heating and break the internal electrical connection and physical contact between the metal armature and the thermal heating element.

2. The volatizer of claim 1, wherein the thermally conductive housing of the case holds the armature in contact with the thermal heating element, and further wherein the electrical connections are electrical prongs.

3. The volatizer of claim 2, wherein the armature and electrical prongs are fixed to the case.

4. The volatizer of claim 2, wherein the armature and electrical prongs have a case retaining means.

5. The volatizer of claim 2, wherein the electrical prongs include two electrical prongs configured to be inserted into an electrical receptacle.

6. The volatizer of claim 2, wherein the electrical prongs are configured to be inserted into a 120V household electrical receptacle.

7. A volatizer comprising:
   a case;
   a first power blade and a second power blade, said power blades being fixed with aspect to the case;
   a first bus bar and a second bus bar, said bus bars being supported by the case;
   a thermal heating element, supported in the case; and
   a resilient and electrically conductive armature spring held in physical contact with at least one of the thermal heating element and a heating element retainer,
   wherein the armature spring, the thermal heating element, and the heating element retainer are configured to be in electrical contact with one another,
   wherein the case is configured to support and heat a volatile material, and
   wherein the case is configured to deform upon excessive heat and function as a thermal cutoff by breaking an internal electrical connection between the armature spring and the at least one of the thermal heating element and the heating element retainer.

8. The volatizer of claim 7, wherein the case is configured to support volatile material selected from a group comprising a liquid, a gel and a liquid impregnated solid.

9. The volatizer of claim 7, wherein the case is configured to support volatile material selected from a group comprising a fragrance, a medicinal, a sanitizer, a deodorant, a pest repellent, a disinfectant, an aroma therapy formulation, a household cleaning material, a perfume, a therapeutic liquid, an insecticide, and a decongestant.

10. The volatizer of claim 7, wherein the first bus bar further comprises:
   the heating element retainer; and
   the armature spring configured to be pressed into a tensioned state by the case, wherein the case holds the armature spring in electrical contact with the heating element retainer.

11. The volatizer of claim 10, wherein, when assembled, the case holds the armature spring in physical contact with the thermal heating element, creating an electrical connection between the armature spring and the thermal heating element.

12. The volatizer of claim 7, wherein during volatizing operation the first power blade makes electrical contact with the first bus bar, the first bus bar makes electrical contact with the thermal heating element, the thermal heating element makes electrical contact with the second bus bar, and the second bus bar makes electrical contact with the second power blade, creating an electrical path from the first power blade to the second power blade.

13. The volatizer of claim 7, wherein there is no electrical path from the first power blade to the thermal heating element until the case is assembled.

14. The volatizer of claim 10, wherein the first power blade is in contact with the armature spring, the armature spring is in contact with the thermal heating element, and the thermal heating element is in contact with the heating element retainer.

15. A fragrance releaser comprising:
   a case configured to deform upon excessive heat and break an internal electrical connection, said case comprising:
   a plug deck including a first power blade and a second power blade; and
   a main housing coupled to the plug deck, said main housing including and supporting a first bus bar, a second bus bar, and a heating element, said first bus bar comprising:
      an armature spring; and
      a heating element retainer;
   wherein the armature spring is held in a tensioned state by an armature spring boss, the armature spring boss pushing the armature spring away from the heating element, and
   wherein the case is configured to support a volatile fragrance, said volatile fragrance being a liquid, a gel or a liquid impregnated solid.

16. The fragrance releaser of claim 15, wherein the power blades are configured to be press fit into the plug deck.

17. The fragrance releaser of claim 15, wherein the main housing further comprises:
   an armature mount;
   a heating element retainer mount; and
   a second bus bar mount.

18. The fragrance releaser of claim 17, wherein the armature spring is configured to be press fit to the armature mount, the heating element retainer is configured to be press fit to the heating element retainer mount, and the second bus bar is configured to be press fit to the second bus bar mount.

19. The fragrance releaser of claim 15, wherein the heating element has a first end and a second end, the second bus bar is configured to receive the second end, the heating element retainer is configured to receive the first end, and the heating element is configured to be press fit into the heating element retainer and the second bus bar.

20. The fragrance releaser of claim 15, wherein the plug deck further comprises:
   an armature spring actuator configured to push the armature spring into physical contact with the heating element when the case is assembled.

21. The fragrance releaser of claim 20, wherein the distance between the armature spring actuator and the heating element is between 0.3 and 0.7 millimeters when the case is assembled.

22. The fragrance releaser of claim 21, wherein the armature spring is formed in an arc such that when the case is assembled the thermal cutoff function will be achieved despite a manufacturing difference of +/−10% in the size of the armature spring actuator, armature spring boss, armature spring mount, heating element retainer mount, plug deck or main housing.

* * * * *